United States Patent

Goettsche et al.

[11] Patent Number: 5,880,143
[45] Date of Patent: Mar. 9, 1999

[54] WOOD PRESERVATIVE

[75] Inventors: Reimer Goettsche, Baden-Baden; Reiner Kober, Fussgönheim; Uwe Kardorff, Mannheim, all of Germany

[73] Assignee: BASF Aktiengesellschaft, Ludwigshafen, Germany

[21] Appl. No.: 836,254

[22] PCT Filed: Nov. 11, 1995

[86] PCT No.: PCT/EP95/04434

§ 371 Date: Aug. 27, 1997

§ 102(e) Date: Aug. 27, 1997

[87] PCT Pub. No.: WO96/15885

PCT Pub. Date: May 30, 1996

[30] Foreign Application Priority Data

Nov. 23, 1994 [DE] Germany .................. 44 41 672.5

[51] Int. Cl.⁶ .............. A01N 43/647; A01N 43/653; A01N 33/04; A01N 37/02
[52] U.S. Cl. ............. 514/383; 514/63; 514/359; 514/384; 514/557; 514/558; 514/560; 514/574; 514/663; 106/18.32; 252/401; 252/403
[58] Field of Search ............... 514/383, 384, 514/239.5, 317, 231.2, 663, 557–558, 560, 574, 359, 63; 106/18.32; 252/401, 403

[56] References Cited

U.S. PATENT DOCUMENTS

| 5,179,116 | 1/1993 | Goettsche et al. ............... 514/388 |
| 5,186,947 | 2/1993 | Goettsche et al. ............... 424/638 |

FOREIGN PATENT DOCUMENTS

| 402 697 | 12/1990 | European Pat. Off. . |
| 466 206 | 1/1992 | European Pat. Off. . |
| 482 433 | 4/1992 | European Pat. Off. . |

OTHER PUBLICATIONS

WPIDS Abstract, accession No. 96–112575, abstracting JP 8–12504 (Jan. 16, 1996).

WPIDS Abstract, accession No. 96–035788, abstracting JP 7–304609 (Nov. 21, 1995).

*Primary Examiner*—John Pak
*Attorney, Agent, or Firm*—Keil & Weinkauf

[57] ABSTRACT

A wood preservative which contains a dimethylalkylamine, an aliphatic $C_8$–$C_{20}$-dicarboxylic acid and a triazole compound.

10 Claims, No Drawings

WOOD PRESERVATIVE

This application is a 371 of PCT/EP95/04434, filed on Nov. 11, 1995.

It is known that dimethylalkylamines, for example in the form of salts of long-chain monocarboxylic acids, can be used for application in oily, solvent-containing wood preservatives (EP 147 976). The same applies to mixtures of fenpropimorph and water-insoluble acids (EP-B-0 402 697).

It is also known that dimethylalkylamine, tridemorph, fenpropimorph or their mixture, an emulsifier and a water-insoluble acid can be used as water-soluble wood preservatives (EP-A-0 370 371).

It is also known that dimethylalkylamine, tridemorph, fenpropimorph, a water-insoluble acid and a water-soluble acid can be used as water-soluble concentrates in wood preservation (DE-A-3 736 298).

Mixtures based on dimethyl-coconut fatty amine, 2-ethylhexanoic acid, propiconazole and an emulsifier have also been described for use as wood preservatives.

However, these water-soluble wood preservatives have considerable disadvantages in application. They have a corrosive effect on iron and steel and dissolve, inter alia, rust and other iron compounds from the surfaces of the impregnation tank with formation of emulsifiable or water-soluble iron salts, so that application solutions acquire a strong brown discoloration in a short time. Consequently, the wood to be impregnated is in turn influenced in its color and is changed, resulting, for example, in a strong gray discoloration owing to reaction of the iron compounds with wood constituents. At the same time, the pH of the appliction solution increases; the result may be instability of the solutions, including phase separation.

It has now been found that the performance characteristics of the water-soluble wood preservatives are considerably improved if wood preservatives which contain a dimethylalkylamine, an aliphatic $C_8$–$C_{14}$-dicarboxylic acid and a triazole compound are used. In addition to the excellent performance characteristics, the wood preservatives have very good activity against wood-destroying Basidiomycetes.

The novel wood preservatives (concentrates) are water-miscible and, on dilution of the concentrates with water, form clear to slightly opaque solutions. Advantageously, the aqueous solutions (impregnating solutions) obtained after dilution of the concentrates with water have a pH of from 4 to 8, preferably from 5 to 7. The aqueous impregnating solutions obtained are distinguished by the fact that the active components penetrate very effectively into the wood to be impregnated and thus result in effective wood preservation.

A dimethylalkylamine is an N,N-dimethyl-N-alkylamine whose alkyl radical contains, for example, 6 to 20 carbon atoms. Dimethylalkylamines having 12 or 14 carbon atoms in the alkyl radical are preferred. In addition to the pure dimethylalkylamines, mixtures, for example mixtures of dimethyl-$C_{12}$-alkylamine and dimethyl-$C_{14}$-alkylamine (dimethyl-($C_{12}/C_{14}$-alkylamine), may also be used.

The novel wood preservatives contain $C_8$–$C_{20}$-dicarboxylic acid, preferably $C_8$–$C_{14}$-dicarboxylic acids. Suitable dicarboxylic acids are, for example, suberic acid, azelaic acid, sebacic acid, undecanedioic acid, dodecanedioic acid, brassylic acid and thapis acid. Sebacic acid is particularly advantageously used.

Examples of suitable triazoles are:

(Z)-2-(1,2,4-triazol-1-ylmethyl)-2-(4-fluorophenyl)-3-(2-chlorophenyl) oxirane (epoxiconazole), 2-(1-chlorocyclopropyl-1-(2-chlorophenyl)-3-(1,2,4-triazol-1-yl)-propan-2-ol, 1-butyl-1-(2,4-dichlorophenyl)-2-(1,2,4-triazol-1-yl) ethanol (hexaconazole), 1-[2-chlorophenyl)methyl]-1-(1,1-dimethyl)-2-(1,2,4-triazol-1-yl-ethanol, 1-(4-fluorophenyl)-1-(2-fluorophenyl)-2-(1,2,4-triazol-1-yl)-ethanol (flutriafol), (RS)-4-(4-chlorophenyl)-2-phenyl-2-(1H-1,2,4-triazol-1-yl-methyl)butyronitrile, 1-[(2 RS, 4 RS;

2 RS, 4 SR)-4-bromo-2-(2,4-dichlorophenyl) tetrahydrofurfuryl]-1H-1,2,4-triazole, 3-(2,4-dichlorophenyl)-2-(1H-1,2,4-triazol-1-yl)quinazolin-4 (3H)-one, (RS)-2,2-dimethyl-3-(2-chlorobenzyl)-4-(1H-1,2,4-triazol-1-yl)butan-3-ol, bitertanol, triadimefon, triadimenol, cyproconazole, dichlobutrazol, difenoconazole, diniconazole, etaconazole, flusilazole, penconazole, tetraconazole, bromuconazole, metconazole, fenbendazol, fensilazol, 1-(2-(2,4,-dichlorophenyl)-1,3-dioxolan-2-ylmethyl)-1H-1,2,4-triazole (azaconazole), 1-(2-(2,4-dichlorophenyl)-4-propyl-1,3-dioxolan-2-yl-methy)-1H-1,2,4-triazole (propiconazole), α-tert-butyl-a-(p-chlorophenylethyl)-H-1,2,4-triazole-1-ethanol (tebuconazole).

Propiconazole, penconazole, cyproconazole, hexaconazole and tebuconazole are particularly advantageously used.

Triazoles may be present not only in the form of the free base but also in the form of a metal salt complex or as an acid addition salt.

In order to improve the fungicidal activity, it may be advantageous if the novel wood preservative additionally contains morpholine derivatives, preferably the fungicidal active ingredients fenpropimorph (4-[3-(4-tert-butylphenyl)-2-methylpropyl]-cis-2,6-dimethylmorpholine), fenpropidin (N-[3(4-tert-butylphenyl)-2-methylpropyl] diperidine or tridemorph (N-tridecyl-2,6-dimethylmorpholine) or salts thereof.

A synergistic improvement in activity is achieved as a result. Fenpropimorph is particularly advantageously used. Fenpropimorph, fenpropidin or tridemorph and the triazoles are preferably used in a weight ratio of from 0.5:1 to 10:1, preferably from 1:1 to 5:1, in particular from 2:1 to 3:1.

It may furthermore be advantageous if the novel wood preservative additionally contains a water-insoluble monocarboxylic acid or a salt thereof.

Suitable water-insoluble monocarboxylic acids are, for example, a straight-chain aliphatic monocarboxylic acid of 5 to 20 carbon atoms, such as hexanoic acid, heptanoic acid, octanoic acid, nonanoic acid or decanoic acid, or a branched aliphatic monocarboxylic acid, such as 2-ethylhexanoic acid, 2-ethylheptanoic acid, isooctanoic acid, isoheptanoic acid, isononanoic acid, versatic acid or neocarboxylic acid (more highly branched monocarboxylic acids). Other water-insoluble monocarboxylic acids, eg. sorbic acid, benzoic acid, or cyclohexanecarboxylic acid, may also be used. 2-Ethylhexanoic acid is particularly advantageously used.

The novel wood preservatives may additionally contain boron compounds, eg. boric acid, alkali metal borates or boric esters, as diffusable components. This additionally results in an improvement in the activity in the protection from blue rot and mold.

The novel wood preservatives (concentrates) contain in general from 5 to 65, in particular from 25 to 55%, by weight of dimethylalkylamine, in particular dimethyl-($C_{12}/C_{14}$) alkylamine, from 0 to 35, in particular from 5 to 20%, by weight of morpholine derivatives, in particular fenpropimorph, from 0.25 to 15, preferably from 1 to 10, in particular from 2.5 to 7.5%, by weight of triazole, from 2.5 to 35, in particular from 10 to 25%, by weight of aliphatic $C_8$–$C_{20}$-dicarboxylic acids, in particular sebacic acid, from 0 to 30, in particular from 2.5 to 12.5%, by weight of water-insoluble monocarboxylic acids, from 0 to 30% by weight of water and from 0 to 30% by weight of organic solvents, the sum in each case being 100% by weight. Water and solvents serve here, inter alia, for better handling, for example adjustment of the viscosity, acceleration of the dissolution of the concentrates in water. Some of the solvents are simultaneously required for dissolving the triazoles.

The concentrates obtained may be present in liquid homogeneous form, as a paste or in solid form.

Preferably used organic solvents are water-soluble or water-miscible polar solvents, for example glycols (ethylene glycol, propylene glycol), glycol ethers (ethylene glycol monomethyl ether, ethylene glycol monoethyl ether, glycol ether acetates (butylglycol acetate), N-alkylpyrrolidones (N-methylpyrrolidone), alcohols, dimethylformamide, acethylformamide and dimethyl sulfoxide.

Hydroxycarboxylic acids, eg. tartaric acid or maleic acid, may be added to the concentrates or impregnating solutions in order to establish the pH, for example of about 6 or lower.

In order to increase the action spectrum or to achieve special effects, for example additional protection from insects including termites, the abovementioned formulations may be combined with further active ingredients, which, if required, are incorporated with suitable additional emulsifiers.

Suitable components of the mixture are, for example, the following compounds:

sulfenamides, such as dichlofluanid, tolylfluanid, folpet, fluorfolpet;

benzimidazoles, such as carbendazim, benomyl, fuberidazoles, thiabendazoles or salts thereof;

thiocyanates, such as thiocyanatomethylthiobenzothiazole, methylene bisthiocyanate, quaternary ammonium compounds, such as benzyldimethyltetradecylammonium chloride, benzyldimethyldodecylammonium chloride or didecyldimethylammonium chloride;

quaternary phosphonium compounds;

iodine derivatives, such as diiodomethyl p-tolyl sulfone, 3-iodo-2-propinyl alcohol, 4-chlorophenyl-3-iodopropargylformal, 3-bromo-2,3-diiodo-2-propenyl ethyl carbonate, 2,3,3-triiodoallyl alcohol, 3-bromo-2,3-diiodo-2-propenyl alcohol, 3-iodo-2-propynyl-n-butyl carbamate, 3-iodo-2-propynyl-n-hexyl carbamate, 3-iodo-2-propinylcyclohexyl carbamate, 3-iodo-2-propynylphenyl carbamate, 0-1-(6-iodo-3-oxohex-5-ynyl)-butyl carbamate, [sic], 0-1-(6-iodo-3-oxohex-5-ynyl)phenyl carbamate [sic], napcocide; phenol derivatives, such as tribromophenol, tetrachlorophenol, tetrachlorophenol [sic], 3-methyl-4-chlorophenol, dichlorophen, o-phenylphenol, m-phenylphenol, p-phenylphenol, 2-benzyl-4-chlorophenol;

bromine derivatives, such as 2-bromo-2-nitro-1,3-propanediol, 2-bromo-2-bromomethylglutaronitrile;

isothiazolinones, such as N-methylisothiazolin-3-one, 5-chloro-N-methylisothiazolin-3-one, 4,5-dichloro-N-octyl-isothiazolin-3-one, N-octylisothiazolin-3-one;

benzisothiazolinones, such as 4,5-trimethylisothiazol-3-one;

pyridines, such as 1-hydroxy-2-pyridinethione (and their Na, Fe, Mn and Zn salts), tetrachloro-4-methylsulfonylpyridine;

metal soaps, such as tin, copper and zinc naphthenate, octoate, 2-ethylhexanoate, oleate, phosphate and benzoate.

Organotin compounds, for example tributyltin (TBT) compounds, dialkyldithiocarbamates, such as Na and Zn salts of dialkyldithiocarbamates, tetramethylthiuram disulfide;

nitriles, such as 2,4,5,6-tetrachloroisophthalodinitrile;

benzothiazoles, such as 2-mercaptobenzothiazole;

quinolines, such 8-hydroxyquinoline and Cu salts thereof;

tris-N-(cyclohexyldiazeniumdioxy)aluminum, N-(cyclohexyl-diazeniumdioxy)tributyltin or K salt, bis-N-(cyclohexyldiazeniumdioxy)copper.

The following may be preferably added as insecticides:

phosphoric esters, such as azinphos-ethyl, azinphos-methyl, 1-(4-chlorophenyl)-4-(0-ethyl, S-propyl) phosphoryloxypyrazole [sic] chlorpyrifos, coumaphos, demeton, demeton-S-methyl, diazinon, dichlorvos, dimethoate, ethoprophos, etrimfos, fenitrothion, fenthion, heptenophos, parathion, parathion-methyl, phosalone, phoxim, pirimiphos-ethyl, pirimiphos-methyl, profenofos, prothiofos, sulfprofos, triazophos and trichloron;

carbamates, such as aldocarb, bendiocarb, 2-(1-methylpropyl)phenylmethyl carbamate, butocarboxim, butoxycarboxim, carbaryl, carbofuran, carbosulfan, cloethocarb, isoprocarb, methomyl, oxamyl, primicarb, promecarb, propoxur und thiocarb;

organosilicon compounds, preferably dimethyl(phenyl) silylmethyl 3-phenoxybenzyl ethers, such as dimethyl (4-ethoxyphenyl)silylmethyl 3-phenoxybenzyl ether, or (dimethylphenyl)silylmethyl 2-phenoxy-6-pyridylmethyl ethers, such as dimethyl(9-ethoxyphenyl) silylmethyl 2-phenoxy-6-pyridylmethyl ether, or [(phenyl)-3-(3-phenoxyphenyl)propyl] (dimethyl)silanes, e.g. (4-ethoxyphenyl)-[3-(4-fluoro-3-phenoxyphenylpropyl]dimethylsilane; pyrethroids, such as allethrin, alphamethrin, bioresmethrin, byfenthrin, cycloprothin, cyfluthrin, decamethrin, cyhalothrin, cypermethrin, deltamethrin, α-cyano-3-phenyl-2-methylbenzyl 2,2-dimethyl-3-(2-chloro-2-trifluoromethylvinyl)cyclopropane carboxylate, fenpropathrin, fenfluthrin, fenvalerate, flucythrinate, flumethrin, fluvalinate, permethrin, resmethrin and tralomethrin;

nitroimines and nitromethylenes, such as 1-[(6-chloro-3-pyridyl)methyl]-4,5-dihydro-N-nitro-1H-imidazole-2-amine (midacloprid), N-[(6-chloro-3-pyridyl)-methyl-]N'-cyano-N'-methylacetamide.

Depending on the danger to the wood, application for preservation of the wood may be effected, for example:

a) by spraying the wood with the impregnating solution, b) by immersing the wood in the impregnating solution (from dipping to impregnation by the open tank process), c) by impregnating the wood with the aid of pressure differences, for example pressure impregnation or double vacuum impregnation, d) by painting the wood or flooding.

In the case of secondary wood products, for example wood cuts, pulps and other industrial products or cellulose-containing materials which are susceptible to fungal attack, for example intermediates in papermaking, woody annual plants (bargasse rape), the application should be adapted to the technical possibilities.

The activity of the compositions in the area of wood preservation covers, for example:

a) molds (eg. *Aspergillus niger*)

b) soft rot fungi (eg. *Chaetomium globosum*)

c) blue stain fungi (eg. *Pullularia pullulans*)

d) wood-destroying Basidiomycetes (eg. *Serpula lacrymans, Coniophora puteana*).

The application concentration and application rate depend on the degree of danger to the wood, on secondary wood products or the cellulose-containing materials and also on the method of application. Thus, the application concentration of the concentrate in the impregnating solution is in general from 0.1 to 50, preferably from 0.2 to 20%, by weight, and the application rate is, for example, from 0.2 to 40, preferably from 0.5 to 20, kg/m$^3$. In the case of secondary wood products and cellulose-containing materials, the undiluted concentrate is generally used (e.g. plywood, particle boards, bagasse boards).

The examples which follow illustrate the invention.

Experimental setup for corrosion tests

Small dip tanks of structural steel (ST 37) are produced and are sandblasted on the inside, said tanks having the following dimensions: height 11 cm, side length 8 cm each (2 mm thick steel sheets). Surface rust formation is achieved by exposure to rain or by artificial sprinkling with water.

After rinsing out with tap water and drying, these tanks are filled with the application solution (500 ml), the discoloration and the appearance of the solution and of the tank are checked after 7 days, the change in pH is measured and in addition the content of dissolved or emulsified iron is determined analytically after coarser constituents have been filtered off.

The results obtained here were confirmed in practical experiments in dip tanks (e.g. 15,000–20,000 l of the impregnating solutions).

Examples not according to the invention (all % data are % by weight).

EXAMPLE A

| | |
|---|---|
| Dimethyl-($C_{12}/C_{14}$)-alkylamine | 30% |
| Fenpropimorph | 20% |
| Polyoxyethylene(5)coconut-amine | 25% |
| 2-Ethylhexanoic acid | 25% |

Corrosion test: 7 days

Application concentration: 3.5% in water

| pH (20° C.) before the test | pH (20° C.) after the test |
|---|---|
| 6.65 | 7.25 |

ΔpH = +0.6

Appearance of the solution after the test: clear, dark brown

Iron content after the test: 155 mg/l

EXAMPLE B

| | |
|---|---|
| Dimethyl-($C_{12}/C_{14}$)-alkylamine | 42.5% |
| Propiconazole | 7.5% |
| Polyoxyethylene(5)coconut-amine | 20% |
| 2-Ethylhexanoic acid | 30% |

Corrosion test: 7 days

Application concentration: 3.5% in water

| pH (20° C.) before the test | pH (20° C.) after the test |
|---|---|
| 6.90 | 7.50 |

ΔpH = +0.6

Appearance of the solution after the test: clear, dark brown

Iron content after the test: 400 mg/l

EXAMPLE C

| | |
|---|---|
| Dimethyl-($C_{12}/C_{14}$)-alkylamine | 50% |
| Isooctanoic acid | 10% |
| Lactic acid 80% (commercial) | 20% |
| Propylene glycol | 15% |
| Water | 5% |

Corrosion test: 7 days

Application concentration: 3.5% in water

| pH (20° C.) before the test | pH (20° C.) after the test |
|---|---|
| 5.55 | 6.95 |

ΔpH = +1.40

Appearance of the solution after the test: milky, turbid, brown

Iron content after the test: 570 mg/l

EXAMPLE D

| | |
|---|---|
| Dimethyl-($C_{12}/C_{14}$)-alkylamine | 50% |
| 2-Ethylhexanoic acid | 24% |
| Propionic acid | 3% |
| Propylene glycol | 10% |
| Water | 13% |

Corrosion test: 7 days

Application concentration: 3.5% in water

| pH (20° C.) before the test | pH (20° C.) after the test |
|---|---|
| 6.60 | 7.25 |

ΔpH = +0.65

Appearance of the solution after the test: turbid, strong brown color

Iron content after the test: 210 mg/l

EXAMPLE E

| | |
|---|---|
| Dimethyl-($C_{12}$/$C_{14}$)-alkylamine | 50% |
| 2-Ethylhexanoic acid | 24% |
| Methoxyacetic acid | 4.5% |
| Propiconazole | 3.0% |
| Propylene glycol | 10% |
| Water | 8.5% |

Corrosion test: 7 days

Application concentration: 3.5% in water

| pH (20° C.) before the test | pH (20° C.) after the test |
|---|---|
| 6.51 | 7.12 |

ΔpH = +0.61

Appearance of the solution after the test: turbid, brown

Iron content after the test: 195 mg/l

EXAMPLE F

| | |
|---|---|
| Dimethyl-($C_{12}$/$C_{14}$)-alkylamine | 50% |
| 2-Ethylhexanoic acid | 22.5% |
| Lactic acid (commercial) | 7.5% |
| Propylene glycol | 10% |
| Water | 10% |

Corrosion test: 7 days

Application concentration: 3.5% in water

| pH (20° C.) before the test | pH (20° C.) after the test |
|---|---|
| 6.43 | 7.13 |

ΔpH = +0.7

Appearance of the solution after the test: turbid, brown

Iron content after the test: 255 mg/l

Examples according to the invention (all % data are % by weight)

EXAMPLE 1

| | |
|---|---|
| Dimethyl-($C_{12}$/$C_{14}$)-alkylamine | 50% |
| 2-Ethylhexanoic acid | 5.0% |
| Sebacic acid | 20% |
| Propiconazole | 10% |
| Propylene glycol | 10% |
| Water | 5.0% |

Corrosion test: 7 days

Application concentration: 3.5% in water

| pH (20° C.) before the test | pH (20° C.) after the test |
|---|---|
| 6.55 | 6.80 |

ΔpH = +0.25

Appearance of the solution after the test: clear, colorless

Iron content after the test: 1.8 mg/l

EXAMPLE 2

| | |
|---|---|
| Dimethyl-($C_{12}$/$C_{14}$)-alkylamine | 40% |
| 2-Ethylhexanoic acid | 5.0% |
| Sebacic acid | 16% |
| Fenpropimorph | 10% |
| Propiconazole | 3.33% |
| Propylene glycol | 10% |
| Water | 15.67% |

Corrosion test: 7 days

Application concentration: 3.5% in water

| pH (20° C.) before the test | pH (20° C.) after the test |
|---|---|
| 6.45 | 6.69 |

ΔpH = +0.24

Appearance of the solution after the test: clear, slightly yellowish

Iron content after the test: 2.5 mg/l

EXAMPLES 3 to 9

| | |
|---|---|
| Dimethyl-($C_{12}$/$C_{14}$)-alkylamine | 45% |
| 2-Ethylhexanoic acid | 5.0% |
| Sebacic acid | 20% |
| Triazole | 5.0% |
| Propylene glycol | 10% |
| Water | 15% |

Corrosion test: 7 days

Application concentration: 3.5% in water

| Ex. | Triazole | pH before | pH After | ΔpH | Appearance of the solution | Fe content [mg/l] |
|---|---|---|---|---|---|---|
| 3 | Pencona-zole | 6.20 | 6.33 | 0.13 | clear, colorless | 1.6 |
| 4 | Tebucona-zole | 6.19 | 6.35 | 0.16 | clear, colorless | 2.3 |
| 5 | Cyprocona-zole | 6.18 | 6.35 | 0.17 | clear, colorless | 2.1 |
| 6 | Bromocona-zole | 6.18 | 6.36 | 0.18 | clear, slightly yellowish | 4.1 |
| 7 | Systanes | 6.18 | 6.36 | 0.18 | clear, colorless | 2.0 |
| 8 | Difencona-zole | 6.19 | 6.36 | 0.17 | clear, colorless | 2.4 |
| 9 | Flusilazol | 6.17 | 6.34 | 0.17 | clear, colorless | 1.8 |

EXAMPLES 10 to 17

| | |
|---|---|
| Dimethyl-($C_{12}$/$C_{14}$)-alkylamine | 40% |
| Fenpropimorph | 10% |
| 2-Ethylhexanic acid | 5.0% |
| Sebacic acid | 18% |
| Triazole | 5.0% |
| Propylene glycol | 10% |

Water 12%
Corrosion test: 7 days
Application concentration 3.5% in water

| Ex. | Triazole | pH before | After | ΔpH | Appearance of the solution | Fe content [mg/l] |
|-----|----------|-----------|-------|-----|---------------------------|-------------------|
| 10 | Penconazole | 6.17 | 6.28 | 0.11 | clear, very slightly yellowish | 3.6 |
| 11 | Tebuconazole | 6.13 | 6.28 | 0.15 | clear, very slighty yellowish | 2.0 |
| 12 | Cyproconazole | 6.14 | 6.27 | 0.13 | clear, very slightly yellowish | 2.0 |
| 13 | Bromoconazole | 6.13 | 6.30 | 0.17 | clear, slightly yellowish | 2.9 |
| 14 | Systanes | 6.20 | 6.29 | 0.09 | clear, very slightly yellowish | 4.0 |
| 15 | Difenconazole | 6.18 | 6.31 | 0.13 | clear, colorless | 3.2 |
| 16 | Flusilazol | 6.15 | 6.30 | 0.15 | clear, very slightly yellowish | 4.7 |
| 17 | Propiconazole | 6.17 | 6.30 | 0.13 | clear, very slightly yellowish | 3.1 |

We claim:

1. A water-dilutable wood preservative consisting essentially of
   a) from 5 to 65% by weight of a dimethylalkylamine,
   b) from 2.5 to 35% by weight of an aliphatic $C_8$–$C_{14}$-dicarboxylic acid and
   c) from 0.25 to 15% by weight of a triazole compound.

2. The wood preservative of claim 1, which contains sebacic acid as the aliphatic $C_{8-C_{14}}$-dicarboxylic acid.

3. The wood preservative of claim 1, which contains a dimethylalkylamine having 6 to 20 carbon atoms in the alkyl radical.

4. The wood preservative of claim 1, which contains a dimethylalkylamine having 12 carbon atoms in the alkyl radical.

5. The wood preservative of claim 1, which contains propiconazole, penconazole, cyproconazole, hexaconazole or tebuconazole as the triazole compound.

6. A process for preserving wood which comprises: treating the wood with the wood preservative defined in claim 1.

7. An impregnating solution for impregnating wood for preservation from fungi, containing a wood preservative as claimed in claim 1 and additionally water.

8. A process for impregnating wood which comprises: impregnating the wood with an aqueous impregnating solution of the wood preservative defined in claim 1.

9. A process for impregnating wood which comprises: impregnating the wood with an aqueous impregnating solution of the wood preservative defined in claim 1, wherein the dimethylalkylamine contains 14 carbon atoms in the alkyl radical.

10. A process for impregnating wood which comprises: impregnating the wood with an aqueous impregnating solution of the wood preservative defined in claim 1, in which the dimethylalkylamine is a mixture of a dimethylalkylamine containing 12 carbon atoms in the alkyl radical and a dimethylalkylamine containing 14 carbon atoms in the alkyl radical.

* * * * *